US006630170B2

United States Patent
Balkus, Jr. et al.

(10) Patent No.: US 6,630,170 B2
(45) Date of Patent: Oct. 7, 2003

(54) MESOPOROUS COMPOSITIONS AND METHOD OF PREPARATION

(75) Inventors: Kenneth J. Balkus, Jr., The Colony, TX (US); Decio H. Coutinho, Dallas, TX (US)

(73) Assignee: Board of Regents The University of Texas System, Austin, TX (US)

( * ) Notice: Subject to any disclaimer, the term of this patent is extended or adjusted under 35 U.S.C. 154(b) by 16 days.

(21) Appl. No.: 09/845,087

(22) Filed: Apr. 26, 2001

(65) Prior Publication Data

US 2002/0197206 A1 Dec. 26, 2002

(51) Int. Cl.[7] .................................................. A61K 9/14
(52) U.S. Cl. ........................ 424/489; 424/400; 424/489; 424/600; 514/772.4
(58) Field of Search ................................ 424/489, 600, 424/400; 514/772.4

(56) References Cited

U.S. PATENT DOCUMENTS

| 4,278,651 A | * | 7/1981 | Hales ............................. 424/1 |
| 5,057,296 A | * | 10/1991 | Beck ........................... 423/277 |
| 5,102,643 A | * | 4/1992 | Kresge et al. ............... 424/328 |
| 5,234,695 A | | 8/1993 | Hobbs et al. ................ 424/489 |

OTHER PUBLICATIONS

Beck et. al., *J. Am Chem. Soc.*, 114, 10834–10843 (1992).

* cited by examiner

*Primary Examiner*—Thurman K. Page
*Assistant Examiner*—Micah-Paul Young
(74) *Attorney, Agent, or Firm*—Jenkens & Gilchrist, P.C.

(57) ABSTRACT

The present invention encompasses novel mesoporous compositions comprising vitamin E, and methods for their synthesis. The mesoporous compositions are synthesized in a range of conditions to produce varied morphologies including, but not limited, to gyroids, hexagons, hexagonal rods, discs, and spheres.

23 Claims, 14 Drawing Sheets

Degree Two Theta

MESOPOROUS COMPOSITIONS AND METHOD OF PREPARATION

BACKGROUND OF THE INVENTION

1. Technical Field of the Invention

The present invention relates to a mesoporous composition and a method for its synthesis. The invention provides a mesoporous composition of a new category in that the templating molecule used in the synthesis comprises vitamin E. The invention further relates to the synthesis of mesoporous compositions showing controlled morphology. The invention also relates to mesoporous compositions comprising vitamin E for use in drug delivery systems, catalysis and other bioanalytical applications.

2. Description of the Prior Art

Porous substances are generally divided by pore size. For example, those having pore sizes smaller than 2 nm are classified as microporous substances, between 2 and 50 nm are classified as mesoporous substances and larger than 50 nm are classified as macroporous substances. Because of the range of their pore sizes, mesoporous materials are compatible with applications such as separation or sensing of relatively large organic molecules. Typical of the mesoporous materials are amorphous or polycrystalline solids such as pillared clays and silicates. Unfortunately, the pores in these materials are often irregularly spaced and broadly distributed in size.

There is growing interest in the use of inorganic materials as host matrices for bioactive molecules. The principal advantages of such host/guest type materials include the stability and relative inertness of the materials as well as their easy transportation as free flowing powders. Considerable synthetic effort has therefore been devoted to developing molecular sieve frameworks with pore diameters within the mesoporous range, and the development of a series of molecular sieves having a hexagonal array of uniform mesopores has been reported. A group of researchers at Mobil Oil Corporation have reported a series of mesoporous molecular sieves, named MCM-41, in U.S. Pat. Nos. 5,057,296 and 5,102,643, which are fully incorporated by reference. According to these patents, MCM-41 has a structure exhibiting hexagonal arrangement of straight channels, such as a honeycomb, on a silica plate. MCM-41 is synthesized using the cationic type surfactant, quaternary alkyltrimethylammonium salts $[C_nH_{2n+1}(CH_3)_3N^+X^-]$ and various silica sources, like sodium silicates, tetraethyl orthosilicate, or silica gel, under hydrothermal conditions. On the other hand, the mesoporous materials in the SBA series, another group of synthetic mesoporous materials, are synthesized using neutral templates.

MCM-41 synthesis has been proposed to occur through a liquid crystal templating mechanism. Researchers have proposed that the structure is defined by the organization of surfactant molecules into liquid crystals which serve as templates for the formation of the MCM-41 structure. (Beck et. al., J. Am. Chem. Soc. 114, 10834 (1992), fully incorporated by reference herein). In other words, the first step in the synthesis would correspond to the formation of a micellar rod around the surfactant micelle, which in a second step will produce a hexagonal array of rods, followed by incorporation of an inorganic array (like silica, or silica-alumina) around the rodlike structures. That is, in an aqueous solution, surfactants form a liquid crystal structure which is surrounded by silicate ions and the liquid crystal structure is associated with MCM-41 substance via a hydrothermal reaction and then, removed by calcination at a temperature of 500 to 600° C., to prepare MCM-41.

MCM-41 has been actively researched for characterization and application by many laboratories, because their large and uniform pore sizes allow the entry of otherwise sterically hindered molecules. The pore size of MCM-41 can be adjusted in a range of from 1.6 up to 10 nm by modulating the kinds of surfactants or synthesis conditions. Additionally, the easily tailored pore size and compositional variance available, provides a versatile range of materials for applications that span from catalysis to drug delivery.

The mesoporous compositions of the present invention are synthesized using a novel templating molecule, vitamin E, which renders the mesoporous compositions of the present invention unique over those described in the art.

A composition comprising vitamin E and silica is taught in U.S. Pat. No. 5,234,695, which is fully incorporated by reference in the disclosure. The invention contemplates the addition of a flow agent to a water dispersible vitamin E composition, where the flow agent is preferably fumed silica having an average particle size of about 0.1 micron. This composition comprises vitamin E and silica and lacks any definite form i.e., represents an amorphous composition.

The composition of the present invention is unique over the amorphous composition described in U.S. Pat. No. 5,234,695, in that said composition is a mesoporous molecular sieve, displaying definite form.

SUMMARY OF THE INVENTION

It is an object of the present invention to provide novel mesoporous compositions comprising vitamin E. It is another object of the invention to provide methods for synthesizing said novel mesoporous compositions.

The mesoporous compositions are synthesized by using Vitamin E d-α-tocopheryl polyethylene glycol 1000 succinate (vitamin E TPGS) as a structure-directing agent. The mesoporous compositions can be synthesized under specific conditions to produce varied morphologies including, but not limited, to gyroids, hexagons, hexagonal rods, discs, and spheres. The synthesis conditions can be modified to control particle morphology, while maintaining the hexagonal mesoporous structure. These new class of compositions have applications as drug delivery vehicles for vitamin E and other water-insoluble drugs; as a catalyst by fixation of large active complexes in the mesopores; as fiber optic sensors by depositing the mesoporous composition comprising a fluorescent dye at the tip of an optical fiber; and in the preparation of mesoporous membranes for use in separation, fuel cells, and in catalytic membrane reactors.

In accordance with an aspect of the present invention, there is provided a method for preparing a mesoporous composition, comprising the steps of:

(A) dissolving a compound possessing amphipathic properties in a solvent to form a solution;

(B) establishing the pH of the solution of step (A) between 0–3;

(C) adding a silica source to the pH-established solution of step (B) to form a mixture;

(D) aging the mixture of step (C) to form a product; and (E) filtering, washing, and drying the product of step (D).

In accordance with another aspect of the present invention, there is provided a mesoporous composition prepared from a mixture comprising vitamin E TPGS, hydrochloric acid, and a silica source.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the invention presented herein.

DETAILED DESCRIPTION OF ILLUSTRATIVE EMBODIMENTS

Figure 1A:
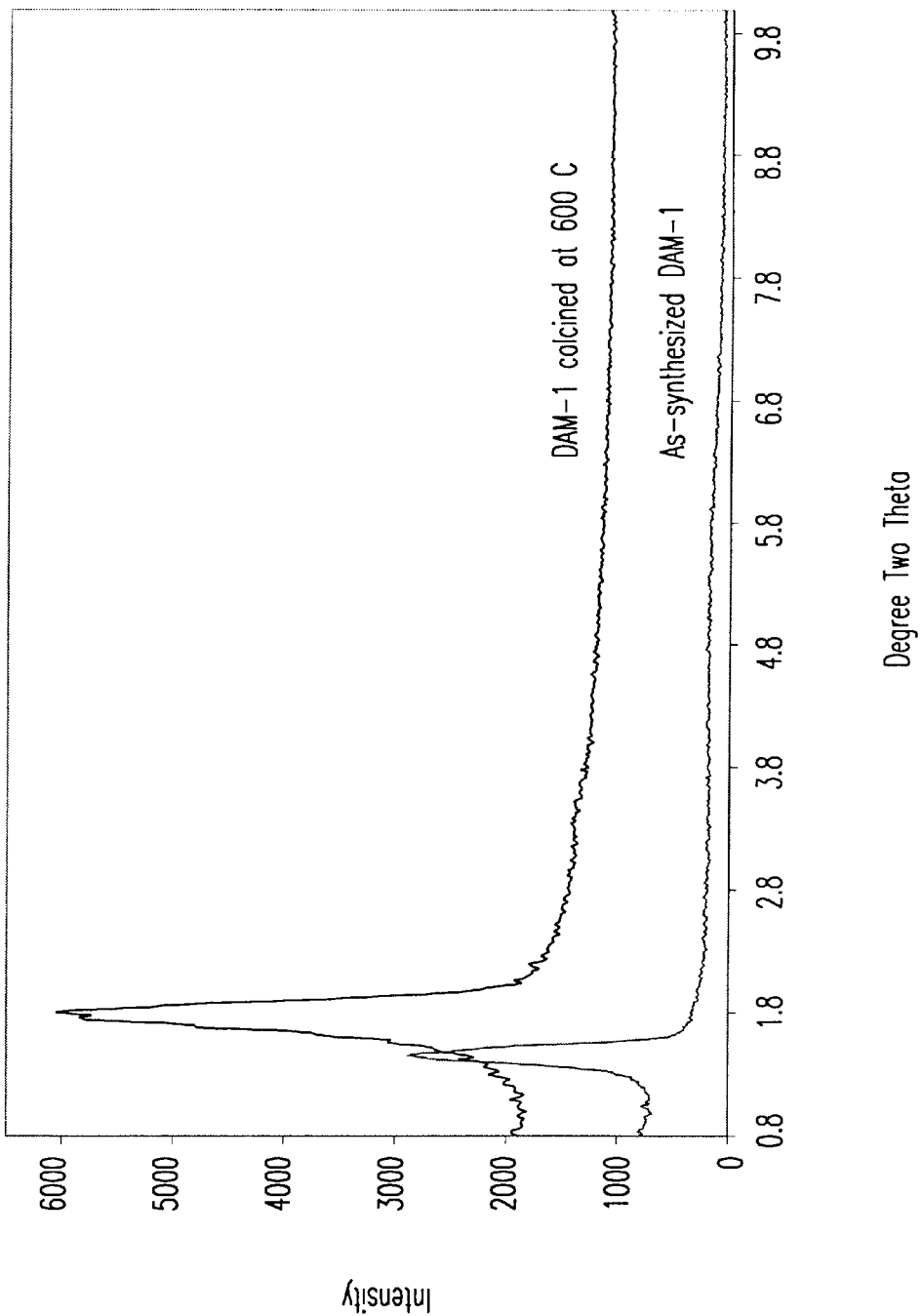
FIG. 1A shows the X-ray powder diffraction (XRD) patterns of the as-synthesized and calcined mesoporous composition prepared by the method discussed in Example 1.
Figure 1B:
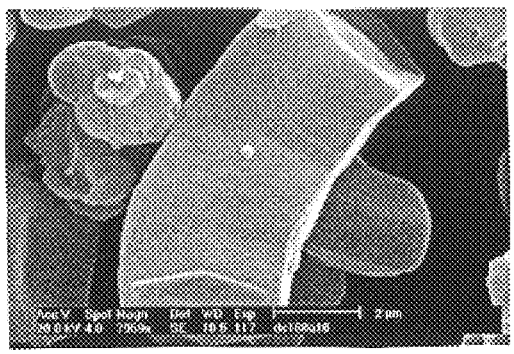
FIGS. 1B–1E are scanning electron micrographs of the mesoporous composition prepared by the method discussed in Example 1.
Figure 1C:
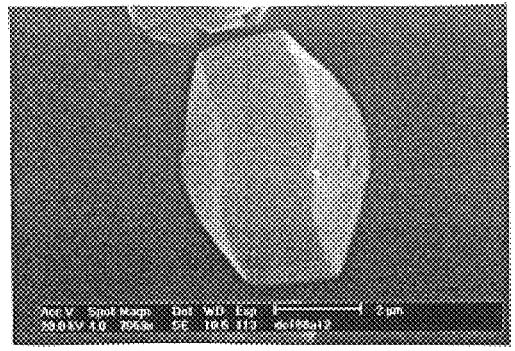
Figure 1D:
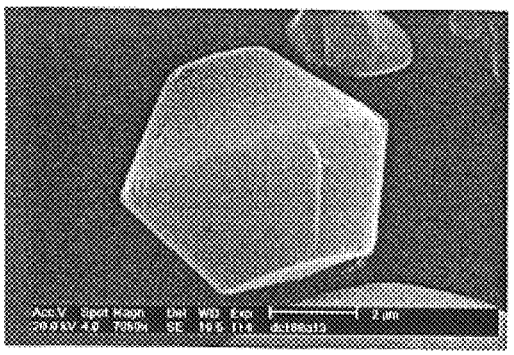
Figure 1E:
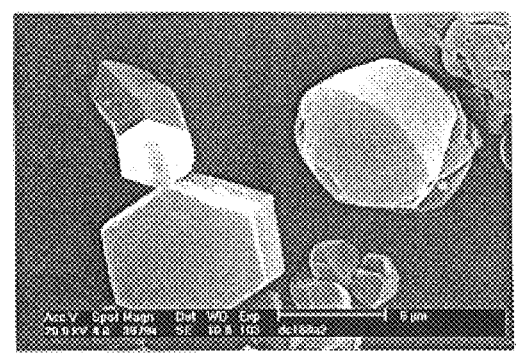
Figure 2A:
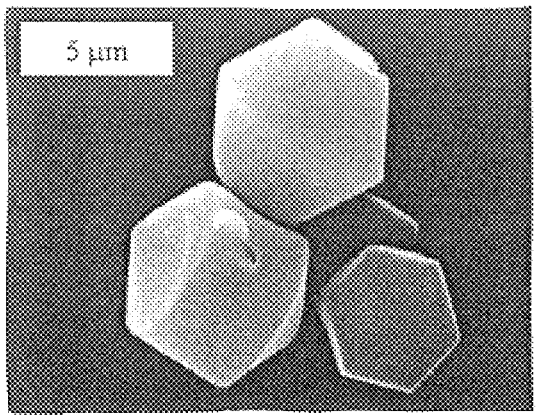
FIGS. 2A–2D are scanning electron micrographs of the mesoporous composition, prepared by the method discussed in Example 2.
Figure 2B:
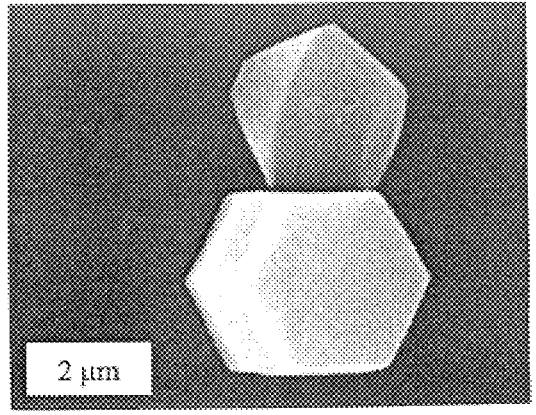
Figure 2C:
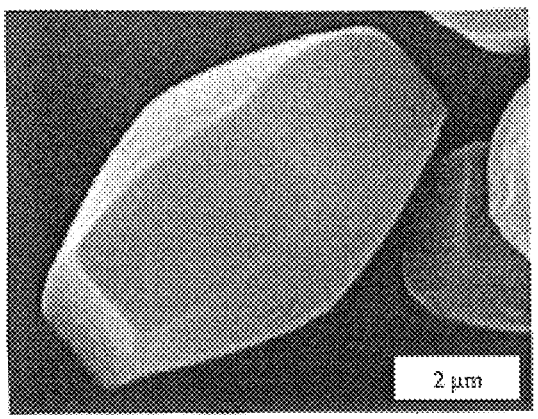
Figure 2D:
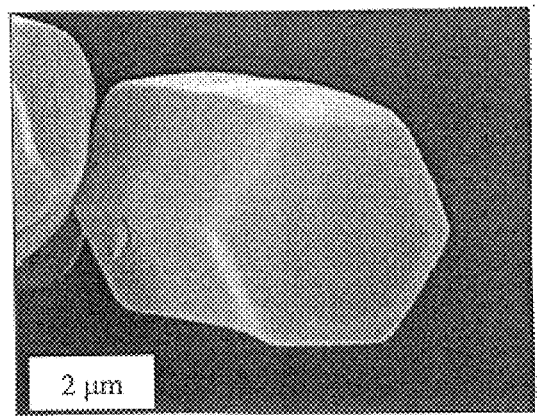

The present invention is generally concerned with novel mesoporous compositions, as well as the methods for synthesizing these mesoporous compositions.

The term "mesoporous composition" as used herein, includes without limitation, those compositions that display pore sizes generally in the range of 2 nm and 50 nm, as well as all compositions produced by the synthesis procedures described herein. In other words, the mesoporous compositions of the present invention are capable of displaying pore sizes that fall outside the 2–50 nm range discussed in the art. The pore sizes can vary depending on the nature of the templating molecule employed in the synthesis of the mesoporous composition of the invention, for example, the length of the polyethylene oxide chains of the templating molecule. The addition of swelling agents to the synthesis mixture can further alter the shape of the micelles, thereby affecting the pore size of the resulting mesoporous composition.

Furthermore, the term "mesoporous composition" as used herein, refers to a composition wherein said composition displays a homogeneity in the pore size i.e., although it is possible to vary pore size between various mesoporous compositions based on the synthesis conditions employed, the pore sizes are homogenous within the context of a specific mesoporous composition.

In accordance with an aspect of the present invention, there is provided a method for preparing a mesoporous composition, comprising the steps of:

(A) dissolving a compound possessing amphipathic properties in a solvent to form a solution;

(B) establishing the pH of the solution of step (A) between 0–3;

(C) adding a silica source to the pH-established solution of step (B) to form a mixture;

(D) aging the mixture of step (C) to form a product; and (E) filtering, washing, and drying the product of step (D).

In accordance with another aspect of the present invention, there is provided a mesoporous composition prepared from a mixture comprising vitamin E TPGS, hydrochloric acid, and a silica source.

The present invention teaches the synthesis of mesoporous compositions, using biomolecules, as templating agents. It is an object of the present invention to provide a mesoporous composition synthesized with functional templates. The term "functional template" as used herein represents a templating molecule used in the synthesis of the mesoporous compositions of the present invention, which in and of itself has a useful function, preferably a useful bioactive or biological function. The bioactive, functional templating molecules used in the synthesis of the mesoporous compositions of the present invention can be used as drugs or drug delivery vehicles.

By way of example, a functional template contemplated by the present invention is a compound comprising vitamin E. In the present invention, the functional template is preferably an alpha-tocopherol polyethylene glycol ester, and more preferably d-alpha-tocopheryl polyethylene glycol succinate (vitamin E TPGS). Vitamin E TPGS is a water soluble derivative of natural source Vitamin E, and has a dual nature, similar to an amphiphile, of hydrophilicity and lipophilicity. The use of the term vitamin E TPGS as used in the specification and the claims, is intended to encompass the compound having the chemical formula $C_{33}O_5H_{54}$ $(CH_2CH_2O)_n$, where "n" represents the number of polyethylene oxide moieties attached to the acid group of crystalline d-alpha tocopheryl acid succinate. Indeed, the chemical structure of the principal component of a commercial preparation of vitamin E TPGS sold by Eastman Chemicals is represented by $C_{33}O_5H_{54}(CH_2CH_2O)_n$ (Eastman® Vitamin E TPGS NF Properties and Applications at http://www.eastman.com/Online_publications/efc226a/efc22602.htm).

The value of "n" in vitamin E TPGS can vary from about 4 to 460, depending on the source of the polyethylene oxide (PEO) moieties used in the preparation of the mesoporous compounds of the present invention. Said sources include, but are not limited to, polyethylene glycol 200 (comprising about 5 PEO moieties), 300 (comprising about 7 PEO moieties), 400 (comprising about 9 PEO moieties), 600 (comprising about 14 PEO moieties), 1000 (comprising about 23 PEO moieties), 6000 (comprising about 136 PEO moieties), 8000 (comprising about 182 PEO moieties), and 20000 (comprising about 455 PEO moieties). By way of example, a form of vitamin E TPGS prepared by esterification of polyethylene glycol 1000 to the acid group of crystalline d-alpha tocopheryl acid succinate, has an "n" value of 23, and is designated as vitamin E TPGS 1000.

Vitamin E TPGS is a surfactant-like amphipathic molecule capable of generating micelles. Amphipathic molecules comprise hydrophilic and hydrophobic surfaces within the same molecule, and therefore readily form micelles. The formation of micelles by vitamin E TPGS enhances its solubility and protects the succinate linkage from hydrolysis in the stomach's acidic environment. Vitamin E TPGS displays distinguishable liquid crystalline phases with increasing water weight percent, and forms hexagonal arrays of micelles at concentrations above its critical micelle concentration of 0.02%.

By using vitamin E TPGS as a template for the synthesis of a mesoporous composition, the present invention results in the synthesis of a free-flowing powder with improved adsorption efficiencies. As a composition of silica with vitamin E, the mesoporous composition of the present invention is different from known molecular sieves. As a mesoporous molecular sieve inclusion compound, the mesoporous composition is different from known compositions of vitamin E and silica. The use of vitamin E TPGS in the synthesis of the mesoporous compositions of the present invention, is provided for exemplary purposes only, and is not intended to limit the scope of the invention. In other words, all forms of vitamin E, which display the micelle-forming ability of vitamin E TPGS, may be used to generate the mesoporous compositions of the present invention.

Furthermore, the scope of the present invention is not intended to be limited solely to the use of vitamin E as a templating molecule. The method of the present invention may be used to synthesize mesoporous compositions comprising templating molecules including, but not limited to all biological and bioactive molecules that are capable of forming micellar structures. Included within said biological and bioactive molecules are molecules with polyethyleneoxide chains attached for water solubility. Exemplary of such molecules are the drugs ADAGEN®, ONCASPAR®, PROTHECAN®, and PEG-Intron®, manufactured by Enzon, Inc.

A silica source is used in the preparation of the mesoporous composition of the present invention. The term "silica source" as used herein, includes without limitation, compounds that produce silicon oxide, $SiO_2$, when subjected to the steps comprising the method for preparation of the mesoporous composition of the present invention (silicon oxide-producing compounds). The "silica source" used in the preparation of the mesoporous composition of the present invention preferably includes triethoxyfluorosilane, tetraethylorthosilicate, and trimethylorthosilicate, either singly or in combination.

The term "silica source" further includes without limitation, metallosilicates i.e., compounds comprising silicon, oxygen, and one or more metals. Without limitation, the metals include, aluminium, titanium, barium, beryllium, calcium, iron, magnesium, manganese, potassium, sodium, or zirconium.

The "silica source" used in the preparation of the mesoporous composition of the present invention further includes organosilanes, which comprise without limitation, $RSiX_3$, $R_2SiX_2$, $R_3SiX$, and $R_4Si$, where "R" represents an organic functional group, and "X" represents a halogen, for example chlorine. The organosilanes further comprise disilanes, including without limitation, $(CH_3CH_2O)_3SiCH_2CH_2Si(CH_3CH_2O)_3$. The organosilanes preferably include, aminopropyltriethoxysilane, 3-mercaptopropyltrimethoxysilane, and phenyltriethoxysilane, either singly or in combination.

The pH of the mixture used in the synthesis of the mesoporous composition of the present invention is established within a range of 0–3. Said pH range is preferably established by the use of an acidic solution. Said pH range is more preferably established by the use of hydrochloric acid.

The aging step used in the preparation of the mesoporous composition of the present invention comprises standing the reaction mixture at a specific temperature for a specific length of time i.e., subjecting the mixture to one or more specific time and temperature combinations or "conditions." Said aging step is preferably carried out between a temperature of 20 to 120° C. and further preferably carried out from between 1 to 100 hours. Said aging step is more preferably carried out under one or more conditions selected from the group consisting of 25–30° C. for 72 hours, 25–30° C. for 48 hours, 90° C. for 24 hours, 25–30° C. for 96 hours, 35–40° C. for 24 hours, 95–100° C. for 48 hours, 40° C. for 20 hours, 90° C. for 48 hours.

Removal of an excess of the organic templating molecule from the mesoporous composition of the present invention may be accomplished by heating (calcination) or solvent extraction. The process of calcination is preferably carried out at a temperature of 500 to 600° C. The process of calcination is further preferably carried out from between 2 to 15 hours. The process of solvent extraction may be carried out with any solvent, more preferably an organic solvent, and most preferably ethanol. The process of solvent extraction is further preferably carried out between 6 to 18 hours.

The method of preparation of the mesoporous compositions of the present invention can be adjusted to modify particle morphology of said mesoporous compositions, while maintaining the hexagonal mesoporous structure. By way of example, acid-catalyzed synthesis at room temperature yields a product comprising particles displaying morphologies of mainly polydisperse spheres with a rugged surface. The addition of ethanol to the acid-catalyzed synthesis changes the particle morphology to hexagons in the 2–5 $\mu$m size range.

The method of preparation of mesoporous compositions of the present invention can be further modified by adding formamide thus increasing the pH to approximately 2.25, thereby producing an array of very well defined shapes including gyroids, hexagonal rods and discs.

Furthermore, the addition of ethanol to the synthesis with formamide yields only spheres in the 2–5 size $\mu$m range, having smooth surfaces.

Another method for changing the morphology of the mesoporous compositions of the present invention, involves the addition of sodium fluoride to the synthesis with formamide. The particle morphology changes to small hexagons in the 1–2 $\mu$m size range.

Furthermore, the addition of compounds that alter the ionic strength of the synthesis mixture, can have an effect on the size of the pores of the mesoporous compositions of the present invention. A change in the ionic strength can also alter the morphology of the mesoporous compositions of the present invention. Without limiting the scope of the invention, examples of compounds that are capable of altering the ionic strength of the synthesis mixture include, but are not limited to, ammonium nitrate, and ammonium chloride. Indeed, because the polyethylene oxide chains of the templating molecule are capable of coiling around cations, the introduction of varying cations in the synthesis mixture can result in a variation in the shape of the micelles formed within a mesoporous composition.

It is believed that all of the attributes of the present invention can be seen in the following examples, which are intended to illustrate, but not limit the scope of the invention.

The chemicals used in the synthesis of the mesoporous compositions of the present invention include tetraethylorthosilicate (TEOS; 98%, Aldrich); Tetramethylorthosilicate (TMOS; 99% Aldrich); 3-aminopropyltrimethoxysilane (ApTMS; 97%, Aldrich); 3-mercaptopropyltrimethoxysilane (MpTMS; 95%, Aldrich); Triethoxyfluorosilane (TEFS; 95%, Gelest); Sodium fluoride (NaF; 99+%, Aldrich); Ammonium fluoride ($NH_4F$; 97%, Aldrich); Ammonium nitrate ($NH_4NO_3$; 98%, Aldrich); Ammonium Chloride ($NH_4Cl$; 99.5%, Aldrich); Hydrochloric acid (HCl; 37%; EM Science); Vitamin E TPGS ($C_{33}O_5H_{54}(CH_2CH_2O)_n$; Eastman Chemicals); Formamide ($HCONH_2$; 99.5%; Aldrich); Ethanol (Reagent grade, Mallinckrodt).

FIG. 1A shows the X-ray powder diffraction (XRD) patterns of the as-synthesized and calcined material produced by the method of example 1 discussed herein. The XRD patterns show a broad low angle reflection with a d-spacing of ~6.05 nm and 4.9 nm respectively. FIGS. 1B–1E show scanning electron micrographs (SEM) of the as-synthesized mesoporous composition produced by the method of example 1 discussed herein. The composition is synthesized at room temperature and comprises hydrochloric acid, formamide, vitamin E, and TEOS. Three distinct morphologies are observed in the product: gyroids, hexagonal rods (short and long), and discoids. In addition, the micrographs show a varied particle size distribution for the mesoporous compositions in the micrometer size range.

FIGS. 2A–2D show scanning electron micrographs of the as-synthesized mesoporous composition prepared at room temperature, followed by heating at 90° C. under static conditions. The compositions synthesized by the method discussed in example 2 comprise hydrochloric acid, formamide, vitamin E and TEOS. The mesoporous compositions display similar morphologies to those observed in FIGS. 1A–1D.

Figure 3A:
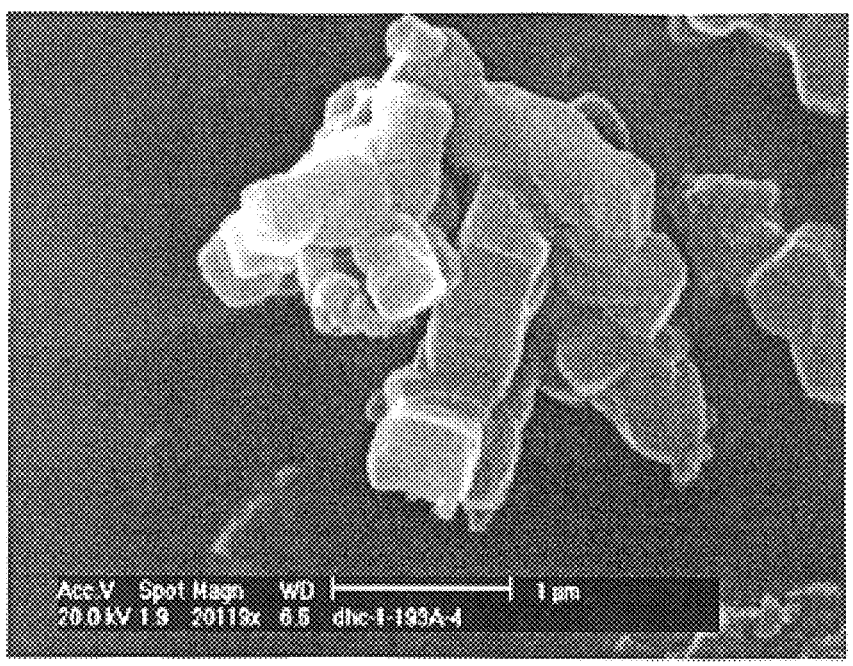
FIGS. 3A and 3B are scanning electron micrographs of the mesoporous composition, prepared by the method discussed in Example 3.
Figure 3B:
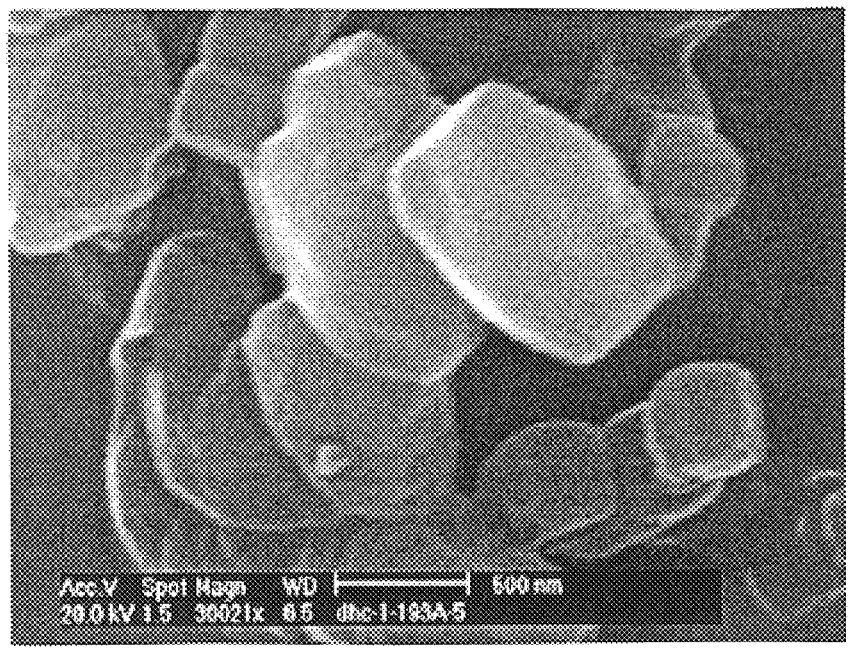

FIGS. 3A and 3B display the scanning electron micrographs of the mesoporous composition produced by the method of example 3, which involves the addition of sodium fluoride to the room temperature synthesis discussed in example 1. The mesoporous composition thus synthesized, is composed of hexagonal small particles in the 1–2 $\mu$m size range.

Figure 4A:
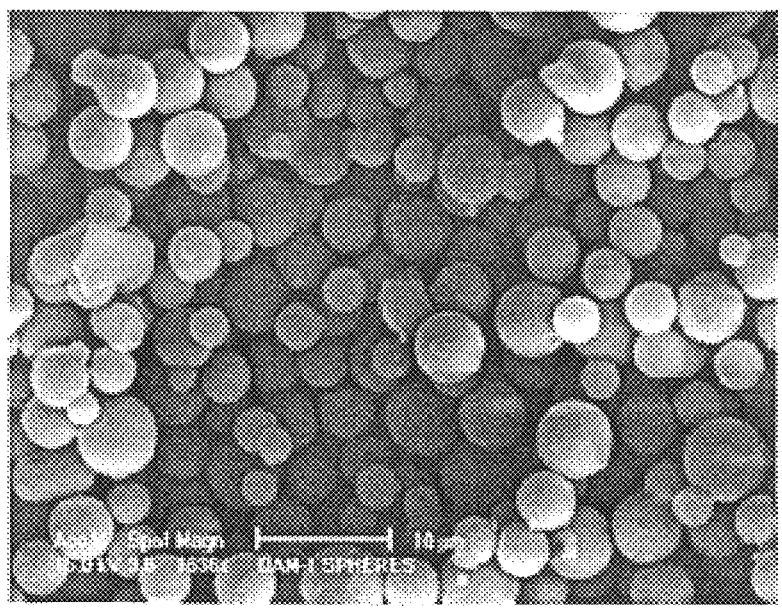
FIGS. 4A and 4B are scanning electron micrographs of the mesoporous composition, prepared by the method discussed in Example 4.
Figure 4B:
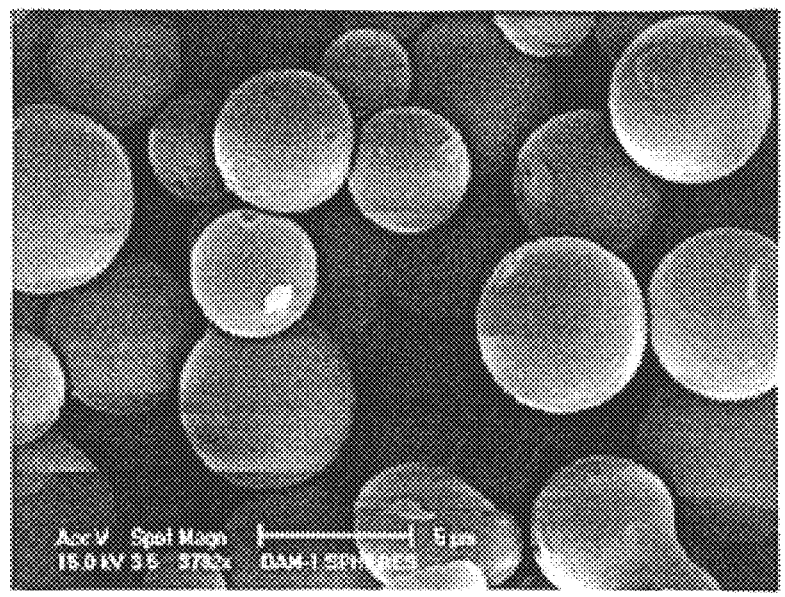

FIGS. 4A and 4B display scanning electron micrographs of the mesoporous compositions synthesized at room temperature, using an ethanol/water mixture to dissolve vitamin E TPGS. The mesoporous composition synthesized by the method of example 4 displays particles with sizes in the 2–5 $\mu$m range.

Figure 5A:
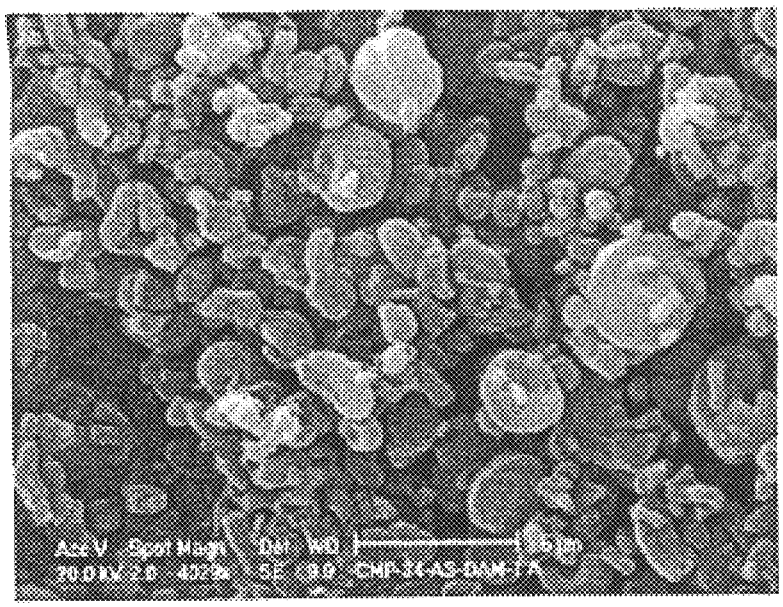
FIGS. 5A and 5B are scanning electron micrographs of the mesoporous composition using (A) ammonium nitrate and (B) ammonium chloride as modifiers prepared by the method discussed in Example 5.
Figure 5B:
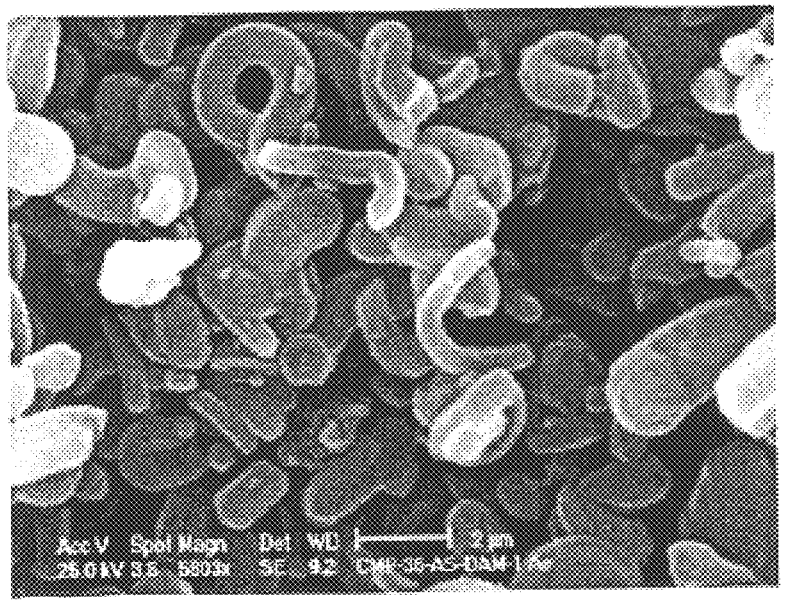

FIGS. 5A and 5B display the scanning electron micrographs of the as-synthesized mesoporous composition produced by the method discussed in example 5, comprising hydrochloric acid, TEOS, vitamin E and an ammonium salt, but lacking formamide. The synthesis with ammonium nitrate produced mostly small particles in the 2–5 $\mu$m range (FIG. 5A) and the synthesis with ammonium chloride produced hexagonal rods of varying length and diameter (FIG. 5B).

Figure 6:
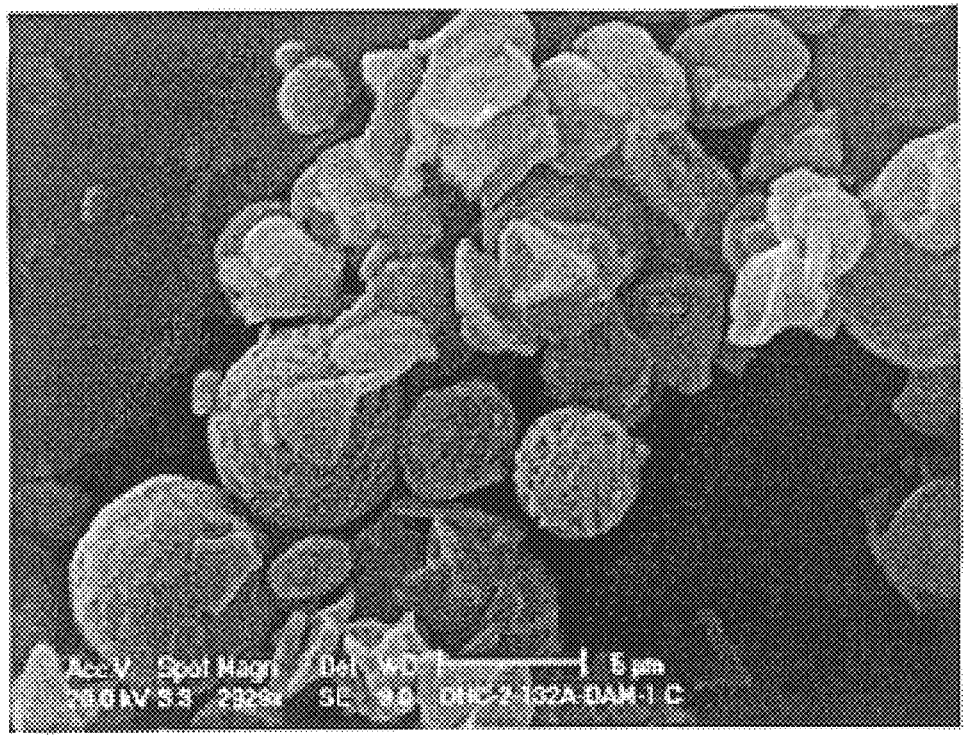
FIG. 6 is a scanning electron micrograph of the mesoporous composition, prepared by the method discussed in Example 6.

FIG. 6 displays a scanning electron micrograph of the composition produced by the method discussed in example 6, showing varied morphologies, including a large number of spheres of diameter in the 2–10 $\mu$m range. The mesoporous composition of example 6 lacks formamide, and comprises hydrochloric acid, vitamin E and TEOS.

Figure 7A:
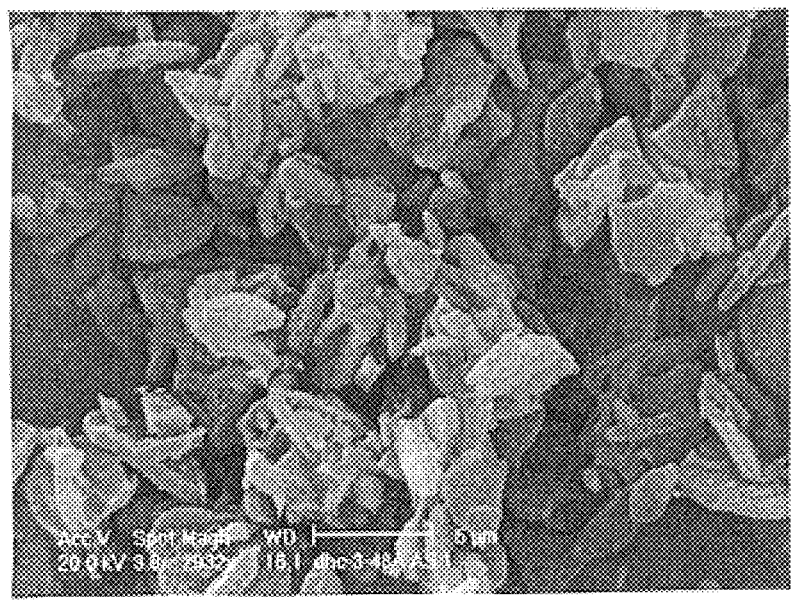
FIGS. 7A and 7B are scanning electron micrographs of the mesoporous composition, using (A) tetraethylorthosilicate and (B) tetramethylorthosilicate as the silica source, and prepared by the method discussed in Example 7.
Figure 7B:
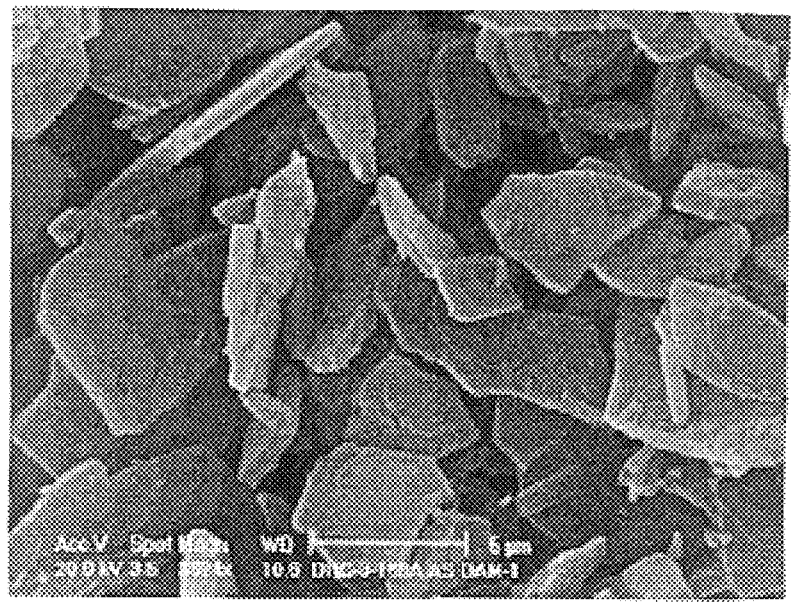

FIGS. 7A and 7B display the scanning electron micrograph of the as-synthesized mesoporous composition produced by the method of example 7 using either TEOS or TMOS as the silica source respectively. Formamide is excluded from the synthesis, which involves a heating step at 95–100° C.

Figure 8A:
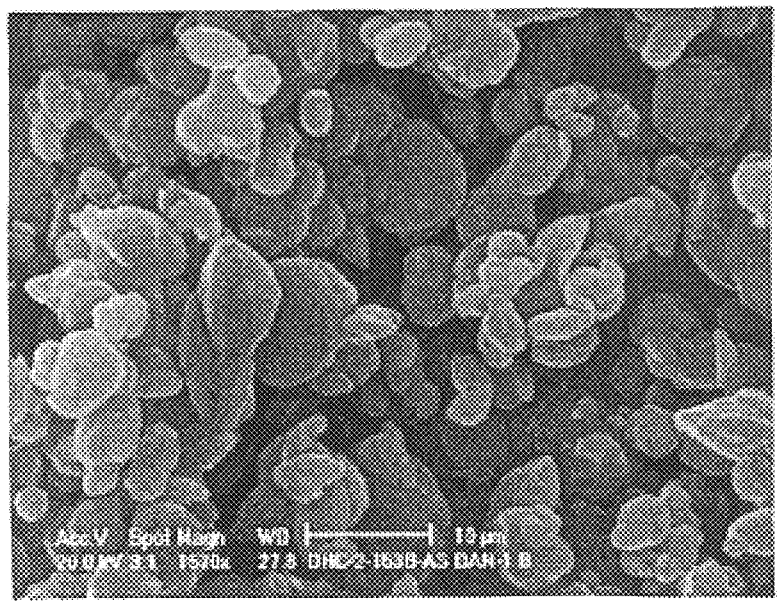
FIGS. 8A and 8B are scanning electron micrographs of the mesoporous composition prepared by the method discussed in Example 8.
Figure 8B:
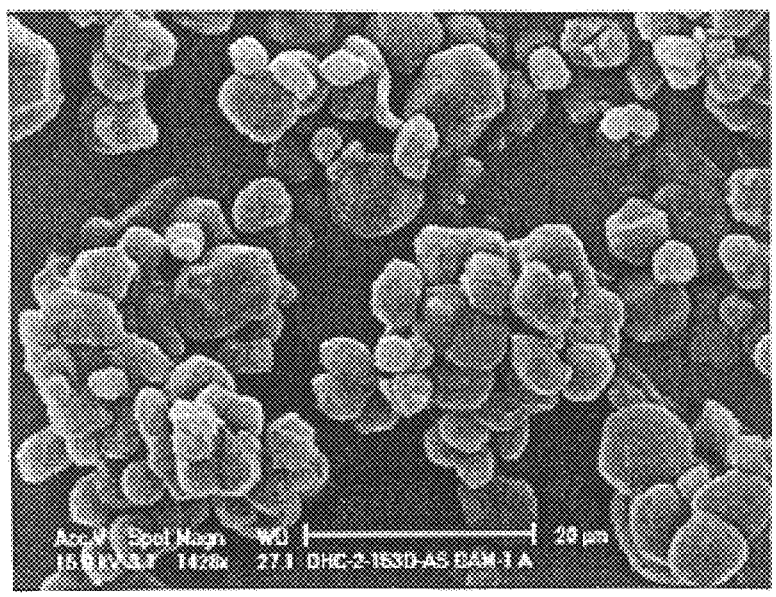

FIGS. 8A and 8B represent the scanning electron micrographs of the mesoporous compositions prepared by the method discussed in example 8. As seen in the figures, the compositions display hexagonal clusters. The mesoporous composition produced in example 8 comprises hydrochloric acid, vitamin E, TEOS and ethanol.

Figure 9:
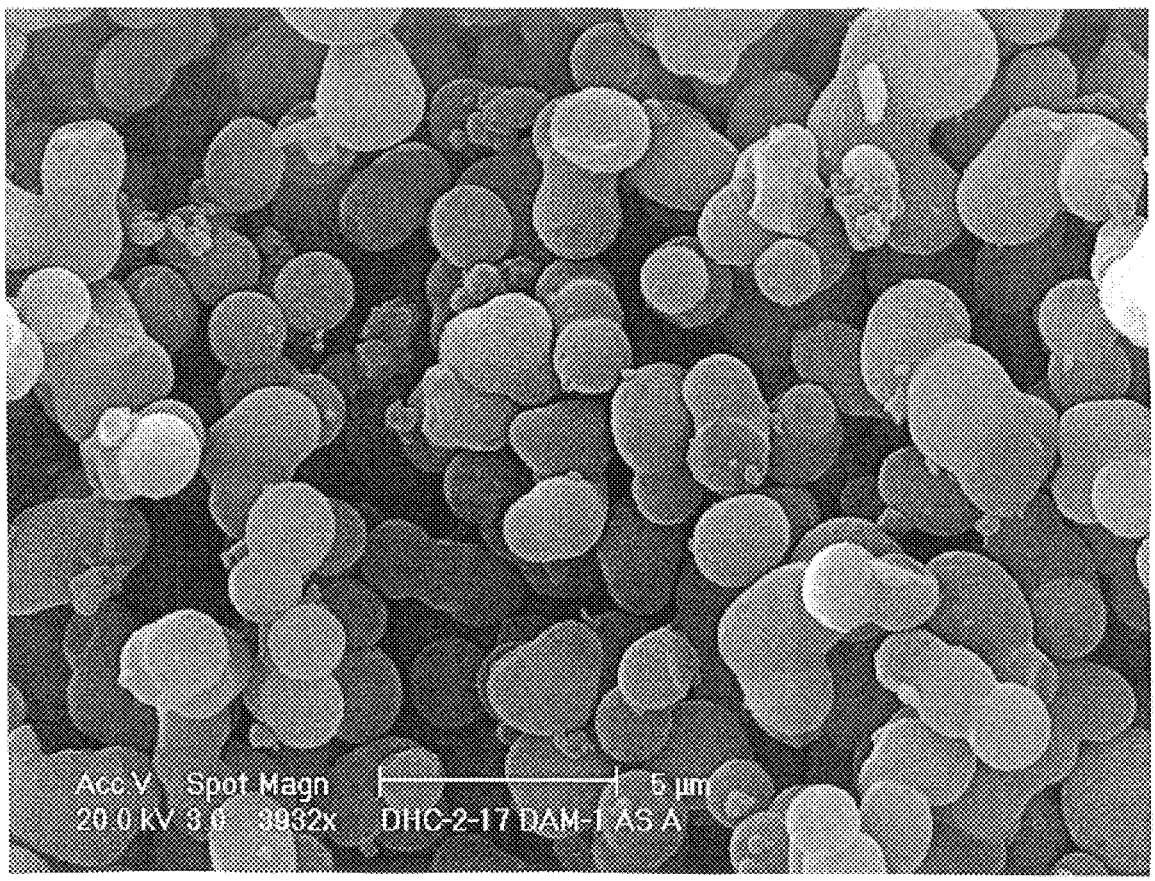
FIG. 9 is a scanning electron micrograph of the mesoporous composition obtained by the method discussed in Example 9.

FIG. 9 shows the scanning electron micrograph of the mesoporous composition obtained by the method discussed in Example 9. The synthesis takes places at room temperature, and involves the addition of sodium fluoride. The mesoporous composition thereby produced, displays a generally spheroid morphology ranging in size from 1–3 $\mu$m, and comprises hydrochloric acid, vitamin E, sodium fluoride, and TEOS.

Figure 10A:
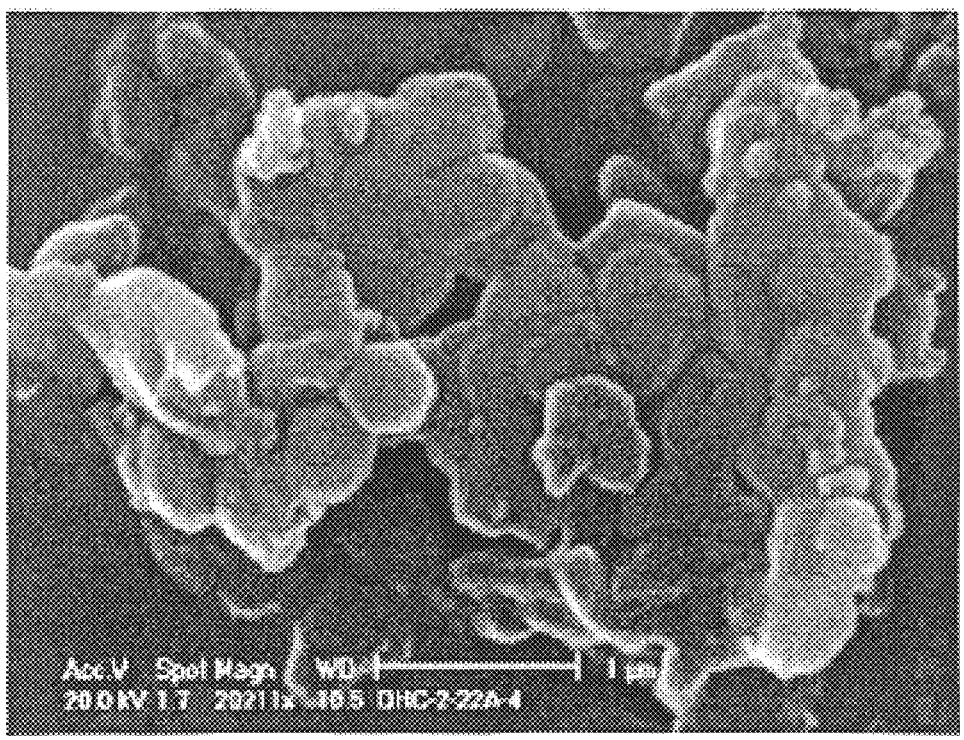
FIG. 10A is a scanning electron micrograph of the mesoporous composition prepared by the method discussed in Example 10.
Figure 10B:
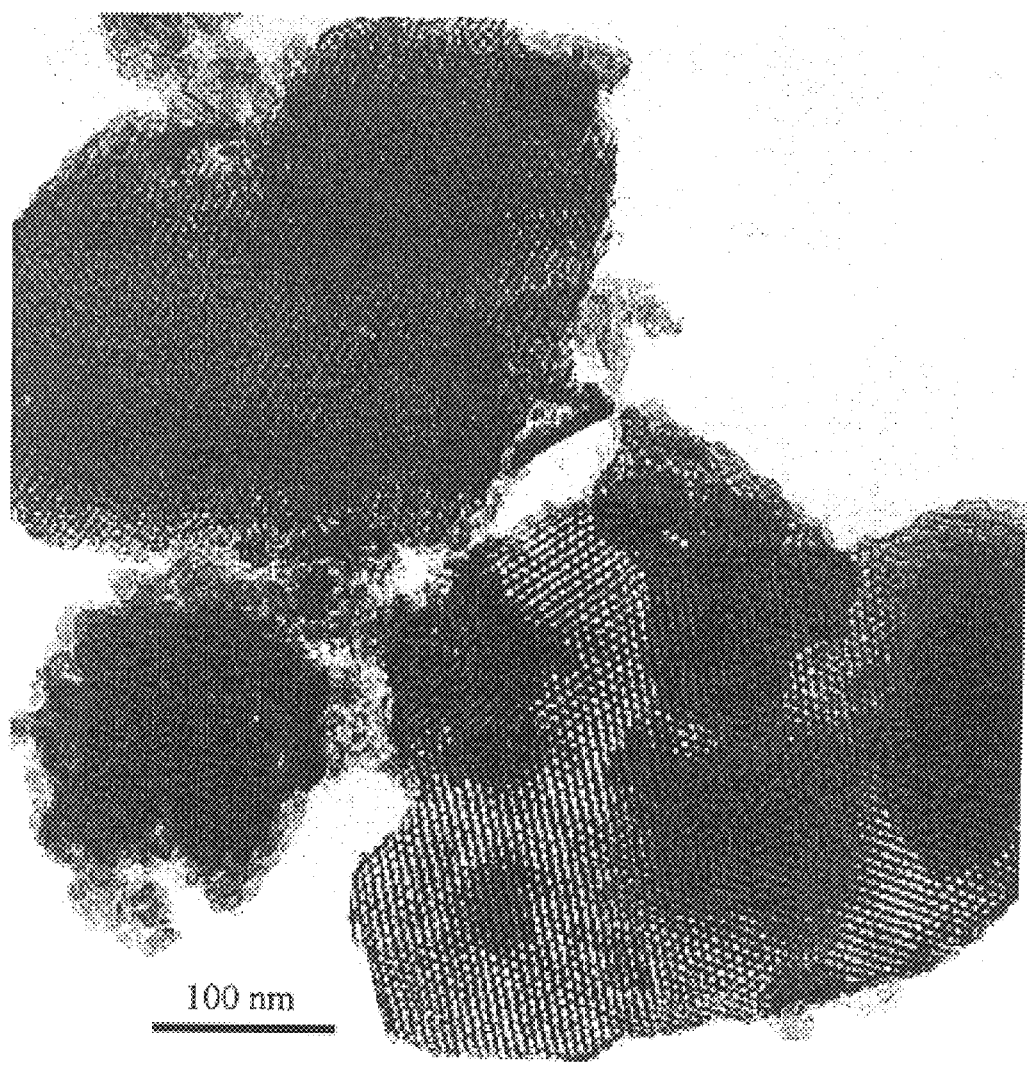
FIG. 10B is a transmission electron micrograph of the mesoporous composition prepared by the method discussed in Example 10.

FIG. 10A shows a scanning electron micrograph of the as-synthesized mesoporous composition using triethoxyfluorosilane (TEFS) as the silica source. The synthesized particles are mainly composed of small hexagons in the 1–2 micrometers size range, and comprise hydrochloric acid, formamide, vitamin E, and TEFS. The transmission electron micrograph of the composition (FIG. 10B) shows that the mesoporous composition synthesized with pure TEFS consists of a highly ordered hexagonal mesostructure.

Figure 11:
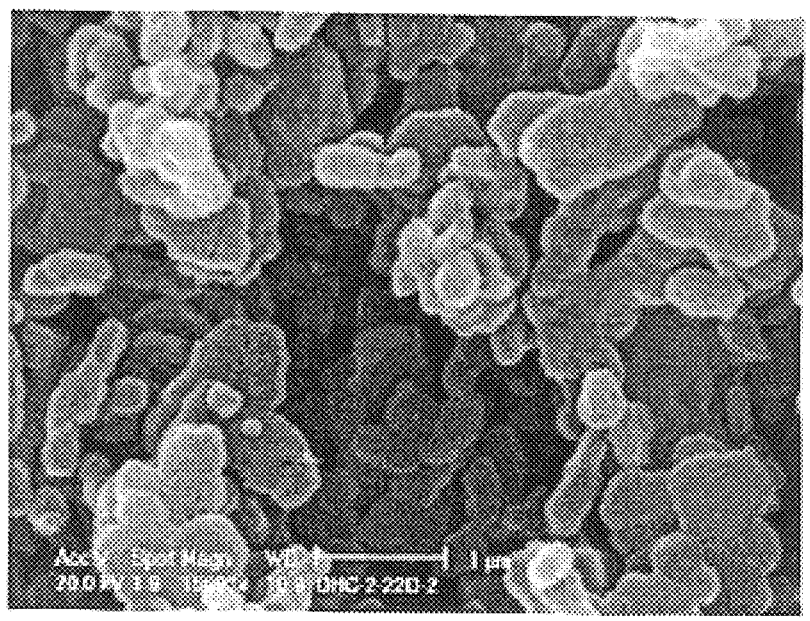
FIG. 11 is a scanning electron micrograph of the mesoporous composition prepared by the method discussed in Example 11.

FIG. 11 displays a scanning electron micrograph of the as-synthesized mesoporous composition synthesized by the method of Example 11. The mesoporous composition synthesized by this method comprises both TEOS and TEFS, in addition to hydrochloric acid, formamide, and vitamin E.

Figure 12:
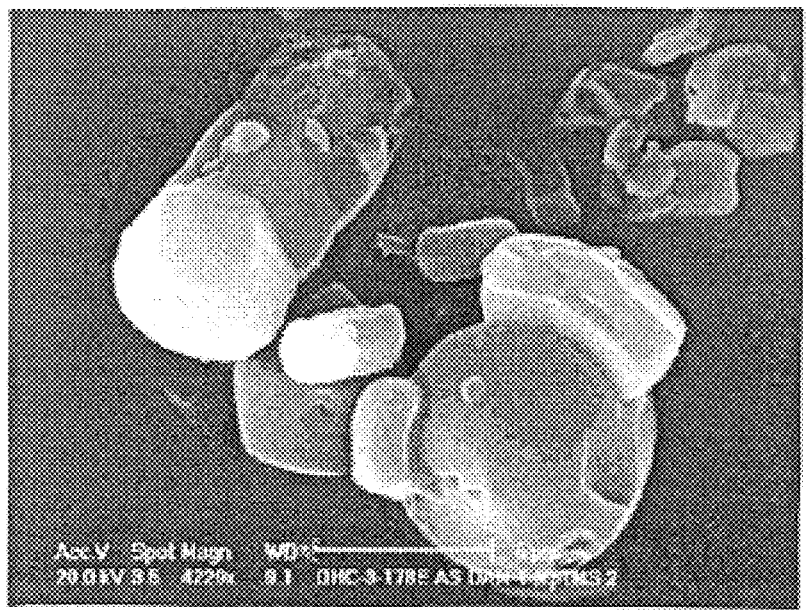
FIG. 12 is a scanning electron micrograph of the mesoporous composition prepared by the method discussed in Example 12.

FIG. 12 displays a scanning electron micrograph of the as-synthesized mesoporous composition synthesized by the method discussed in example 12. The synthesis involves the use of ApTMS and MpTMS, in addition to TMOS, as silica sources. The composition synthesized by this method comprises water, hydrochloric acid, formamide, vitamin E, TMOS, ApTMS, and MpTMS.

Figure 13:
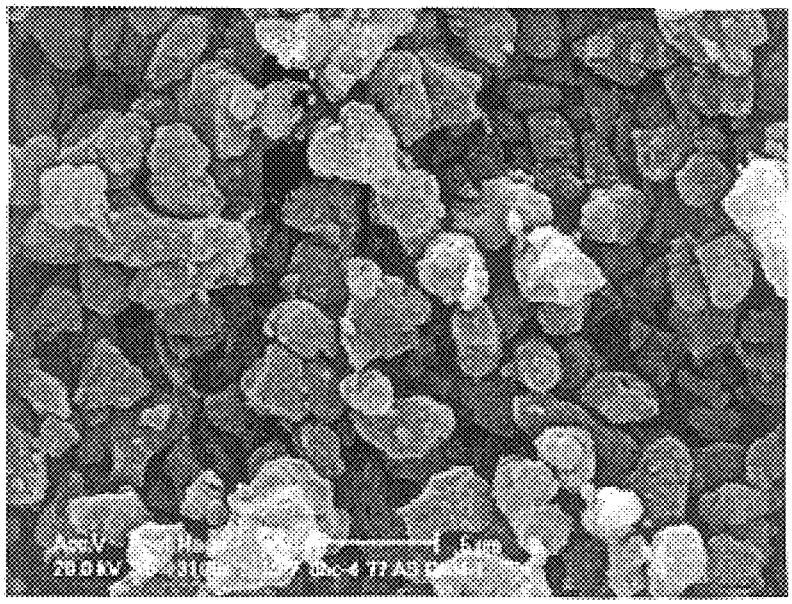
FIG. 13 is a scanning electron micrograph of the mesoporous composition prepared by the method discussed in Example 13.

FIG. 13 displays a scanning electron micrograph of the as-synthesized mesoporous composition synthesized by the method discussed in example 13. The synthesis is similar to that discussed in example 12, except that formamide is left out of the synthesis mixture, and the aging process takes place at 40° C. for 20 hours, followed by heating at 90° C. for 48 hours.

Figure 14:
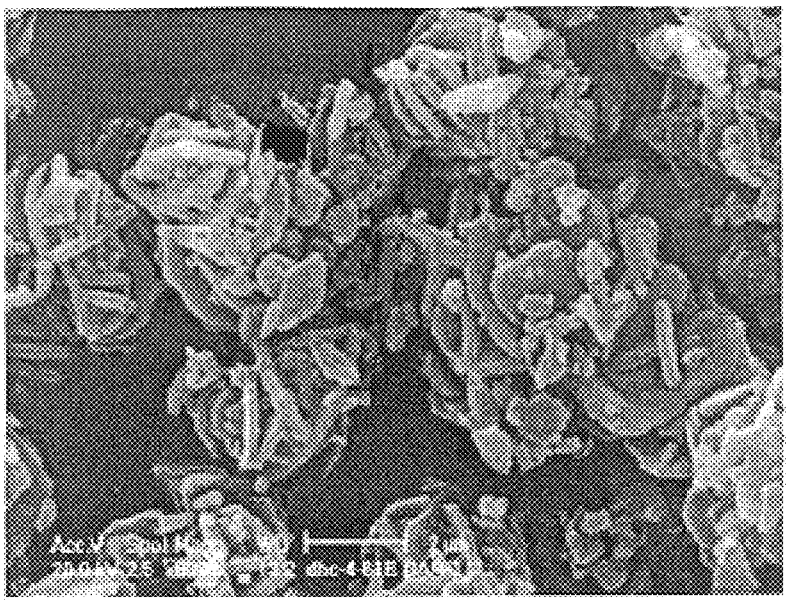
FIG. 14 is a scanning electron micrograph of the mesoporous composition prepared by the method discussed in Example 14.

FIG. 14 displays a scanning electron micrograph of the as-synthesized mesoporous composition synthesized by the method discussed in example 14. The synthesis involves the addition of ammonium fluoride to the mixture of example 13.

WORKING EXAMPLES

Example 1

This example illustrates the preparation of the mesoporous composition of the invention at room temperature.

Vitamin E TPGS was stirred in deionized water until completely dissolved to give a 3.45% by weight solution. To this mixture, 12M hydrochloric acid and formamide were added and the mixture was stirred for 48 hours at room temperature. Finally tetraethylorthosilicate (TEOS) was added and the mixture was stirred for approximately five minutes. The final gel (pH 2.24) of molar composition 100 water: 7.25 hydrochloric acid: 14.5 formamide: 0.031 vitamin E TPGS: 0.13 TEOS was aged at room temperature (i.e., 25–30° C.) under static conditions for 72 hours. The process of "aging" comprises standing the gel at a specific temperature for a specific length of time i.e., subjecting the gel to one or more specific time and temperature combinations or "conditions." The resulting white powder was suction filtered, washed with deionized water and dried at room temperature for 12 hours. Calcination was performed by heating the product to 600° C. for 6 hours. Calcination is the process by which the organic template is removed from the inorganic composition. It comprises a step of heating the composition to be calcined, to a high temperature until all of the organic templates have been removed. FIG. 1A shows the X-ray powder diffraction (XRD) patterns of the as-synthesized and calcined mesoporous composition. The XRD patterns show a broad low angle reflection with a d-spacing of ~6.05 nm and 4.9 nm respectively. FIGS. 1B–1E show scanning electron micrographs (SEM) of the as-synthesized mesoporous composition. Three distinct morphologies were observed in the product: gyroids, hexagonal rods (short and long), and discoids. After calcination at 600° C., particle morphology is maintained. In addition, the micrographs show a range of particle size distributions for the mesoporous compositions in the micrometer size range.

Example 2

This example illustrates the synthesis of the mesoporous composition of the invention at room temperature followed by 90° C. heating under static conditions. Vitamin E TPGS was stirred in deionized water until completely dissolved to give a 3.45% by weight solution. To this mixture, 12M hydrochloric acid and formamide were added and the mixture was stirred for 48 hours at room temperature. Finally TEOS was added and the mixture was stirred for approximately five minutes. The final gel of molar composition 100 water: 7.25 hydrochloric acid: 14.5 formamide: 0.031 vitamin E TPGS: 0.13 TEOS was aged at room temperature under static conditions for 48 hours, followed by 24 hours at 90° C. under static conditions. The resulting white powder was suction filtered, washed with ethanol and then dried at 90° C. for 12 hours. The product was then calcined at 500° C. in air for 12 hours. FIGS. 2A–2D show scanning electron micrographs of the as-synthesized mesoporous composition displaying the same morphologies as in Example 1.

Example 3

This example illustrates the morphology transformation caused by the addition of sodium fluoride to the synthesis discussed in Example 1. Vitamin E TPGS was dissolved in water after which 12M hydrochloric acid, formamide and sodium fluoride were added and stirred for 48 hours at room temperature giving a 3.45% by weight. TEOS was added and the final gel of molar composition 100 water: 7.25 hydrochloric acid: 14.38 formamide: 0.031 Vitamin E TPGS: 0.005 sodium fluoride: 0.13 TEOS was stirred for an additional 5 minutes followed by aging at room temperature for 72 hours. The solids were filtered, washed with deionized water and dried at 90° C. for 12 hours. The compositions were then calcined at 500° C. for 12 hours. FIGS. 3A and 3B display the scanning electron micrographs of the mesoporous composition produced by the method of example 3. The mesoporous composition synthesized is composed of hexagonal small particles in the 1–2 $\mu$m size range.

Example 4

This example describes the room temperature synthesis of the mesoporous composition of the invention exhibiting a spherical morphology. Vitamin E TPGS was dissolved in a 12–35% (w/w) ethanol/water solution to give a 3.53% by weight solution. To this mixture, 12M hydrochloric acid and formamide were added and stirred for 48 hours at room temperature. Finally, TEOS was added and stirred for ~5 minutes. The final gel of molar composition (518–684) water: 54.4 hydrochloric acid: 108.5 formamide: 0.23 vitamin E TPGS: (27–93) ethanol:1 TEOS was aged at room temperature under static conditions for 96 hours. The resulting white powder was suction filtered, washed with deionized water and dried at 90° C. for 12 hours. The product was then calcined to 500° C. for 12 hours. FIGS. 4A and 4B display scanning electron micrographs of the mesoporous compositions synthesized by the method discussed in example 4 showing particle sizes in the 2–5 $\mu$m range. Additionally, the micrographs show that after calcination the shape of the particles is maintained.

Example 5

This example illustrates the synthesis of the mesoporous composition of the invention using ammonium nitrate and ammonium chloride as modifiers as modifiers. Vitamin E TPGS was dissolved in a 0.013M hydrochloric acid solution to give a 2.3% by weight solution. To this solution, ammonium nitrate or ammonium chloride was added and stirred for ~20 minutes. Finally, TEOS was added and stirred for ~5 minutes. The final gel (pH 1.9) was aged at room temperature for 48 hours followed by 24 hours at 90° C. Table 1 contains the molar composition of these syntheses. The resulting white powder was suction filtered, washed with deionized water and dried at 90° C. for 12 hours.

TABLE 1

Molar Composition of the Composition Synthesized in Example 5

| | Water | Hydrochloric acid | TEOS | Vitamin E TPGS | $NH_4Cl$ | $NH_4NO_3$ |
|---|---|---|---|---|---|---|
| Mole Ratio | 100 | 0.023 | 0.140 | 0.028 | 0.99 | |
| Mole Ratio | 100 | 0.023 | 0.140 | 0.028 | | 1.32 |

FIGS. 5A and 5B display the scanning electron micrographs of the as-synthesized mesoporous composition produced by the method discussed in this example. The synthesis with ammonium nitrate produced mostly small particles in the 2–5 $\mu$m range (FIG. 5A) and the synthesis with ammonium chloride produced hexagonal rods of varying length and diameter (FIG. 5B).

Example 6

This example illustrates the room temperature synthesis of the mesoporous composition of the invention without formamide. Vitamin E TPGS was stirred in deionized water until completely dissolved to give a 1.96% by weight solution. To this mixture, 12M hydrochloric acid was added and stirred for ~20 minutes after which TEOS was added and stirred for an additional 20 minutes. The final gel of molar composition 100 water: 1.17 hydrochloric acid: 0.023 vitamin E TPGS: 0.41 TEOS was aged at room temperature for 48 hours under static conditions. The white solid was suction filtered, washed with deionized water and dried at 90° C. for 12 hours. The white free-flowing powder was calcined at 500° C. for ~12 hours. FIG. 6 displays a scanning electron micrograph of the composition produced by the method discussed in example 6, showing varied morphologies, including a large number of spheres of diameter in the 2–10 μm range.

Example 7

This example illustrates the synthesis of the mesoporous composition of this invention without formamide at 95–100° C. Vitamin E TPGS was stirred in deionized water until completely dissolved to give a 1.96% by weight solution. To this mixture, 12M hydrochloric acid was added and stirred for ~20 minutes after which TEOS or TMOS was added and stirred for an additional 20 minutes. The final gel (see Table 2 for molar composition) was aged at 35–40° C. for ~24 hours under static conditions followed by heating to 95–100° C. for an additional 48 hours. The slightly yellow colored product was suction filtered, washed with deionized water and dried at 90° C. for 12 hours. The product was calcined at 500° C. for ~12 hours. FIGS. 7A and 7B display the scanning electron micrograph of the as-synthesized mesoporous composition produced by the method of example 7 using TEOS and TMOS as the silica source respectively.

TABLE 2

Molar Composition of the Composition Synthesized in Example 7

|  | Water | Hydrochloric acid | Vitamin E TPGS | TEOS | TMOS |
|---|---|---|---|---|---|
| Mole Ratio | 100 | 1.17 | 0.023 | 0.57 |  |
| Mole Ratio | 100 | 1.17 | 0.023 |  | 0.57 |

Example 8

The morphology of the particles produced in example 6 can be modified by the addition of ethanol to the synthesis mixture. Ethanol was added to the water/hydrochloric acid/vitamin E mixture and stirred for 5 minutes. TEOS was then added to the mixture, which was stirred for an additional 10 minutes. The final gel of molar composition 100 water: 1.46 hydrochloric acid: 7.43 Ethanol: 0.027 Vitamin E TPGS: 0.49 TEOS was allowed to stand at room temperature for 3 days. The white solid was suction filtered, washed with water and dried at 90° C. overnight. The free-flowing powder was then calcined at 500° C. for 12 hours. The scanning electron micrographs display hexagonal clusters as shown in FIGS. 8A and 8B.

Example 9

This example illustrates the room temperature synthesis of the mesoporous compositions of the invention using sodium fluoride. Vitamin E TPGS was stirred in deionized water until completely dissolved to give a 1.96% by weight solution. To this mixture, 12M hydrochloric acid was added and stirred for ~20 minutes after which TEOS was added and stirred for an additional 20 minutes. The final gel of molar composition 100 water: 1.17 hydrochloric acid: 0.023 vitamin E TPGS: 0.022 sodium fluoride: 0.41 TEOS was aged at room temperature for 48 hours under static conditions. The white powder was suction filtered, washed with deionized water and dried at 90° C. for 12 hours. The white powder was calcined at 500° C. for 12 hours. FIG. 9 shows the scanning electron micrograph of the mesoporous composition obtained by the method discussed in Example 9. The composition displays a generally spheroid morphology ranging in size from 1–3 μm.

Example 10

This example illustrates the synthesis of the mesoporous compositions of this invention using triethoxyfluorosilane (TEFS) as the silica source. Vitamin E TPGS was stirred in deionized water until completely dissolved to give a 3.45% by weight solution. To this mixture, 12M hydrochloric acid and formamide were added and stirred for 24 hours at room temperature. Finally, TEFS was added and the mixture was stirred for ~5 minutes. The final gel of molar composition 100 water: 7.4 hydrochloric acid: 14.4 formamide: 0.03 vitamin E TPGS: 0.15 TEFS was aged at room temperature and static conditions for 3 days. The resulting white powder was washed with deionized water, suction filtered and dried at 90° C. for 12 hours. The product was then calcined to 500° C. for 12 hours. FIG. 10A shows a scanning electron micrograph of the as-synthesized mesoporous composition. The particles are mainly composed of small hexagons in the 1–2 micrometers size range. The transmission electron micrograph of the composition (FIG. 10B) shows that the mesoporous composition synthesized with pure TEFS consists of a highly ordered hexagonal mesostructure.

Example 11

This example illustrates the synthesis of the mesoporous compositions of this invention using both TEOS and TEFS as sources of silica. Vitamin E TPGS was stirred in deionized water until completely dissolved to give a 3.45% by weight solution. To this mixture, 12M hydrochloric acid and formamide were added stirred for 48 hours at room temperature. A 40% (w/w) TEFS and 60% (w/w) TEOS was prepared and added to the water/hydrochloric acid/formamide/vitamin E mixture, stirred for ~10 minutes, and allowed to age at room temperature for 72 hours. The gel of molar composition 100 water: 7.4 hydrochloric acid: 14.4 formamide: 0.03 vitamin E TPGS: 0.08 TEOS: 0.06 TEFS was aged at room temperature and static conditions for 3 days. The resulting white powder was filtered, washed with deionized water, and dried at 90° C. for 12 hours. The product was then calcined at 500° C. for 12 hours. FIG. 11 displays a scanning electron micrograph of the as-synthesized mesoporous composition synthesized by the method of Example 11.

Example 12

This example shows the preparation of the mesoporous compositions of the invention with amine and thiol functional groups. Vitamin E TPGS was stirred in deionized water until completely dissolved to give a 3.45% by weight solution after which 12M hydrochloric acid and formamide were added and the mixture was stirred for 48 hours at room temperature. Finally, a mixture of trimethylorthosilicate (TMOS), 3-aminopropyltriethoxysilane (ApTMS) and 3-mercaptopropyltrimethoxysilane (MpTMS) was added and the mixture was stirred for additional 10 minutes. The final gel (pH 2.3) was allowed to age at room temperature for 4 days. Table 3 contains the molar compositions and the mole fraction of each silica source in the starting mixture. The resulting white powder was filtered, washed with deionized water, and dried at 90° C. for 12 hours. Excess vitamin E TPGS template was removed by stirring ~300 mg of the white powder in ~30 ml of ethanol for ~12 hours. FIG. 12 displays a scanning electron micrograph of the as-synthesized mesoporous composition synthesized by the method discussed in example 12.

TABLE 3

Molar composition of the Composition Synthesized in Example 12

|   |               | $H_2O$ | HCl | $HCONH_2$ | Vit E TPGS | TMOS | ApTMS | MpTMS |
|---|---------------|--------|-----|-----------|------------|------|-------|-------|
| A | Mole Ratio    | 100    | 7.3 | 14.4      | 0.031      | 0.12 | 0.010 | 0.010 |
|   | Mole Fraction*|        |     |           |            | 0.85 | 0.07  | 0.07  |
| B | Mole Ratio    | 100    | 7.3 | 14.4      | 0.031      | 0.12 | 0.015 | 0.016 |
|   | Mole Fraction*|        |     |           |            | 0.79 | 0.10  | 0.10  |
| C | Mole Ratio    | 100    | 7.3 | 14.4      | 0.031      | 0.14 | 0.005 | 0.005 |
|   | Mole Fraction*|        |     |           |            | 0.94 | 0.03  | 0.03  |

*Mole fraction of silicon atoms in the initial TMOS/ApTMS/MpTMS mixture.

Example 13

This example shows the preparation of the mesoporous compositions of the invention with amine and thiol functional groups. Vitamin E TPGS was stirred in deionized water until completely dissolved to give a 1.9% by weight solution after which 12M hydrochloric acid was added and the mixture was stirred for ~10 minutes at room temperature. Finally, a mixture of trimethylorthosilicate (TMOS), 3-aminopropyltriethoxysilane (ApTMS) and 3-mercaptopropyltrimethoxysilane (MpTMS) was added and the mixture was stirred for additional 10 minutes. The final gel was allowed to age at 40° C. for 20 hours followed by heating at 90° C. for 48 hours. Table 4 contains the molar compositions and the mole fraction of each silica source in the starting mixture. The resulting solids were filtered, washed with deionized water, and dried at 90° C. for 12 hours. Excess vitamin E TPGS template was removed by stirring ~300 mg of the dried powder in ~30 ml of ethanol for ~12 hours. FIG. 13 displays a scanning electron micrograph of the as-synthesized mesoporous composition synthesized by the method discussed in example 13.

Example 14

This example shows the preparation of the mesoporous compositions of the invention with amine and thiol functional groups using ammonium fluoride. Vitamin E TPGS was stirred in deionized water until completely dissolved to give a 1.9% by weight solution after which 12M hydrochloric acid and ammonium fluoride were added and the mixture was stirred for ~10 minutes at room temperature. Finally, a mixture of trimethylorthosilicate (TMOS), 3-aminopropyltriethoxysilane (ApTMS) and 3-mercaptopropyltrimethoxysilane (MpTMS) was added and the mixture was stirred for additional 30 minutes at room temperature. The final gel was allowed to age at 40° C. for 20 hours followed by heating at 90° C. for 48 hours. Table 5 contains the molar compositions and the mole fraction of each silica source in the starting mixture. The resulting solids were filtered, washed with deionized water, and dried at 90° C. for 12 hours. Excess vitamin E TPGS template was removed by stirring ~300 mg of the dried powder in ~30 ml of ethanol for ~12 hours. FIG. 14 displays a scanning electron micrograph of the as-synthesized mesoporous composition synthesized by the method discussed in example 14.

TABLE 4

Molar Composition of the Composition Synthesized in Example 13

|   |               | Water | Hydrochloric acid | Vitamin E TPGS | TMOS | ApTMS | MpTMS |
|---|---------------|-------|-------------------|----------------|------|-------|-------|
| A | Mole Ratio    | 100   | 3.66              | 0.019          | 0.52 | 0.044 | 0.045 |
|   | Mole Fraction*|       |                   |                | 0.85 | 0.07  | 0.07  |
| B | Mole Ratio    | 100   | 3.66              | 0.019          | 0.50 | 0.032 | 0.031 |
|   | Mole Fraction*|       |                   |                | 0.89 | 0.057 | 0.055 |
| C | Mole Ratio    | 100   | 3.66              | 0.019          | 0.58 | 0.013 | 0.014 |
|   | Mole Fraction*|       |                   |                | 0.96 | 0.021 | 0.02  |

*Mole fraction of silicon atoms in the initial TMOS/ApTMS/MpTMS mixture.

TABLE 5

Molar Composition of the Composition Synthesized in Example 14

| | | Water | Hydrochloric acid | Vitamin E TPGS | Ammonium fluoride | TMOS | ApTMS | MpTMS |
|---|---|---|---|---|---|---|---|---|
| A | Mole Ratio | 100 | 0.062 | 0.022 | 0.005 | 0.49 | 0.010 | 0.010 |
| | Mole Fraction* | | | | | 0.96 | 0.020 | 0.019 |
| B | Mole Ratio | 100 | 0.062 | 0.022 | 0.004 | 0.45 | 0.029 | 0.028 |
| | Mole Fraction* | | | | | 0.89 | 0.057 | 0.055 |

*Mole fraction of silicon atoms in the initial TMOS/ApTMS/MpTMS mixture.

What is claimed is:

1. A mesoporous composition prepared from a mixture comprising hydrochloric acid, vitamin E and a silica source, wherein said vitamin E functions as a templating molecule, and said mesoporous composition exhibits uniform pore size.

2. The composition of claim 1, wherein said mixture further comprises one or more compounds selected from the group consisting of formamide, sodium fluoride, ethanol, ammonium nitrate and ammonium chloride.

3. The composition of claim 1, wherein the silica source is selected from the group consisting of triethoxyfluorosilane, tetraethylorthosilicate, trimethylorthosilicate, 3-aminopropyltriethoxysilane, 3-mercaptopropyltrimethoxysilane and mixtures thereof.

4. A mesoporous composition prepared from a mixture comprising hydrochloric acid, formamide, vitamin E TPGS and tetraethylorthosilicate in the ratio 7.25:14.4:0.03:0.13 respectively.

5. A mesoporous composition prepared from a mixture comprising hydrochloric acid, formamide, vitamin E TPGS, sodium fluoride and tetraethylorthosilicate in the ratio 7.25:14.38:0.031:0.005:0.13 respectively.

6. A mesoporous composition prepared from a mixture comprising hydrochloric acid, formamide, vitamin E TPGS, ethanol and tetraethylorthosilicate in the ratio 54.4:108.5:0.23:(27–93):1 respectively.

7. A mesoporous composition prepared from a mixture comprising hydrochloric acid, tetraethylorthosilicate, vitamin E TPGS, and ammonium chloride in the ratio 0.023:0.140:0.028:0.99 respectively.

8. A mesoporous composition prepared from a mixture comprising hydrochloric acid, tetraethylorthosilicate, vitamin E TPGS, and ammonium nitrate in the ratio 0.023:0.140:0.028:1.32 respectively.

9. A mesoporous composition prepared from a mixture comprising hydrochloric acid, vitamin E TPGS, and tetraethylorthosilicate in the ratio 1.17:0.023:0.41 respectively.

10. A mesoporous composition prepared from a mixture comprising hydrochloric acid, vitamin E TPGS, and tetraethylorthosilicate in the ratio 1.17:0.023:0.57 respectively.

11. A mesoporous composition prepared from a mixture comprising hydrochloric acid, vitamin E TPGS, and trimethylorthosilicate in the ratio 1.17:0.023:0.57 respectively.

12. A mesoporous composition prepared from a mixture comprising hydrochloric acid, ethanol, vitamin E TPGS, and tetraethylorthosilicate in the ratio 1.46:7.43:0.027:0.49 respectively.

13. A mesoporous composition prepared from a mixture comprising hydrochloric acid, vitamin E TPGS, sodium fluoride and tetraethylorthosilicate in the ratio 1.17:0.023:0.022:0.41 respectively.

14. A mesoporous composition prepared from a mixture comprising hydrochloric acid, formamide, vitamin E TPGS and triethoxyfluorosilane in the ratio 7.4:14.4:0.03:0.15 respectively.

15. A mesoporous composition prepared from a mixture comprising hydrochloric acid, formamide, vitamin E TPGS, tetraethylorthosilicate and triethoxyfluorosilane in the ratio 7.4:14.4:0.03:0.08:0.05 respectively.

16. A mesoporous composition prepared from a mixture comprising hydrochloric acid, formamide, vitamin E TPGS, trimethylortho silicate, 3-aminopropyltriethoxysilane, and 3-mercaptopropyltrimethoxysilane, in the ratio 7.3:14.4:0.031:0.12:0.010:0.010 respectively.

17. A mesoporous composition prepared from a mixture comprising hydrochloric acid, formamide, vitamin E TPGS, trimethylorthosilicate, 3-aminopropyltriethoxysilane, and 3-mercaptopropyltrimethoxysilane, in the ratio 7.3:14.4:0.031:0.12:0.015:0.016 respectively.

18. A mesoporous composition prepared from a mixture comprising hydrochloric acid, formamide, vitamin E TPGS, trimethylorthosilicate, 3-aminopropyltriethoxysilane, and 3-mercaptopropyltrimethoxysilane, in the ratio 7.3:14.4:0.031:0.12:0.005:0.005 respectively.

19. A mesoporous composition prepared from a mixture comprising hydrochloric acid, vitamin E TPGS, trimethylorthosilicate, 3-aminopropyltriethoxysilane, and 3-mercaptopropyltrimethoxysilane, in the ratio 3.66:0.019:0.52:0.044:0.045 respectively.

20. A mesoporous composition prepared from a mixture comprising hydrochloric acid, vitamin E TPGS, trimethylorthosilicate, 3-aminopropyltriethoxysilane, and 3-mercaptopropyltrimethoxysilane, in the ratio 3.66:0.019:0.50:0.032:0.031 respectively.

21. A mesoporous composition prepared from a mixture comprising hydrochloric acid, vitamin E TPGS, trimethylorthosilicate, 3-aminopropyltriethoxysilane, and 3-mercaptopropyltrimethoxysilane, in the ratio 3.66:0.019:0.58:0.013:0.014 respectively.

22. A mesoporous composition prepared from a mixture comprising hydrochloric acid, vitamin E TPGS, ammonium fluoride, trimethylorthosilicate, 3-aminopropyltriethoxysilane, and 3-mercaptopropyltrimethoxysilane, in the ratio 0.062:0.022:0.005:0.49:0.010:0.010 respectively.

23. A mesoporous composition prepared from a mixture comprising hydrochloric acid, vitamin E TPGS, ammonium fluoride, trimethylorthosilicate, 3-aminopropyltriethoxysilane, and 3-mercaptopropyltrimethoxysilane, in the ratio 0.062:0.022:0.005:0.49:0.010:0.010 respectively.

* * * * *

UNITED STATES PATENT AND TRADEMARK OFFICE
CERTIFICATE OF CORRECTION

PATENT NO. : 6,630,170 B2  Page 1 of 1
DATED : October 7, 2003
INVENTOR(S) : Kenneth J. Balkus, Jr. et al.

It is certified that error appears in the above-identified patent and that said Letters Patent is hereby corrected as shown below:

Column 6,
Line 9, replace "aminopropyltriethoxysilane," with -- 3- aminopropyltriethoxysilane --

Column 12,
Line 11, replace "for 12 hours." with -- for ~12 hours. --

Signed and Sealed this

Thirteenth Day of January, 2004

JON W. DUDAS
*Acting Director of the United States Patent and Trademark Office*